(12) United States Patent
Brown et al.

(10) Patent No.: US 8,580,564 B2
(45) Date of Patent: Nov. 12, 2013

(54) BIOMIMETIC CELL SCAFFOLDS

(75) Inventors: Robert Brown, Middlesex (GB); Umber Cheema, Middlesex (GB); Sandy MacRobert, London (GB); Ektoras Hadjipanayi, Middlesex (GB)

(73) Assignee: UCL Business PLC, London (GB)

(*) Notice: Subject to any disclaimer, the term of this patent is extended or adjusted under 35 U.S.C. 154(b) by 36 days.

(21) Appl. No.: 12/991,396

(22) PCT Filed: May 7, 2009

(86) PCT No.: PCT/GB2009/001158
§ 371 (c)(1),
(2), (4) Date: Dec. 6, 2010

(87) PCT Pub. No.: WO2009/136173
PCT Pub. Date: Nov. 12, 2009

(65) Prior Publication Data
US 2011/0070646 A1    Mar. 24, 2011

Related U.S. Application Data

(60) Provisional application No. 61/051,124, filed on May 7, 2008.

(51) Int. Cl.
*C12N 5/00* (2006.01)

(52) U.S. Cl.
USPC ............................ 435/377; 435/325; 435/366

(58) Field of Classification Search
None
See application file for complete search history.

(56) References Cited

U.S. PATENT DOCUMENTS

2005/0027356 A1* 2/2005 Fishman et al. ............. 623/6.63

FOREIGN PATENT DOCUMENTS

WO    2006/003442    1/2006

OTHER PUBLICATIONS

Karageorgiou et al., Porosity of 3D bion1 aterial scaffolds and osteogenesis, Biomaterials 26 (2005) 5474-5491.*
Tang et al., Fabrication of collagen gels that contain patterned, micrometer-scale cavities, Adv. Mater. 2004, 16, No. 15, Aug. 4.*
Guenat et al., Development of an Array of Ion-Selective Microelectrodes Aimed for the Monitoring of Extracellular Ionic Activities, Anal. Chem. 2006, 78, 7453-7460.*
Keenan et al. Biomolecular gradients in cell culture systems, Lab Chip, 2008, 8, 34-57.*
Bianco et al, Stem cells in tissue engineering, Nature, vol. 414, Nov. 1, 2001.*
Downing et al., The influence of microtextured basal lamina analog topography on keratinocyte function and epidermal organization, J Biomed Mater Res 72A: 47-56, 2005.*
Nelson, Microstructured extracellular matrices in tissue engineering and development, Current Opinion in Biotechnology 2006, 17:518-523.*

(Continued)

*Primary Examiner* — Jim Ketter
*Assistant Examiner* — Reza Ghafoorian
(74) *Attorney, Agent, or Firm* — Bozicevic, Field & Francis LLP; Pamela J. Sherwood

(57) ABSTRACT

This invention relates to biomimetic implants containing mammalian cells which are induced by their environment to produce gradients of diffusible factors. This may be useful in eliciting a physiological pro-angiogenic response which stimulates angiogenesis and revascularisation in tissue adjacent the implant, for example in therapeutic applications in which increased angiogenesis and/or vasculogenesis is required. This may also be useful in providing biomimetic mammalian cell niches for cell culture and differentiation.

10 Claims, 13 Drawing Sheets

(56) References Cited

OTHER PUBLICATIONS

Bezuidenhout; et al., "Effect of well defined dodecahedral porosity on inflammation and aniogenesis", ASAIO Journal (2002), 48(5):465-471.

Cheema; et al., "Spatially defined oxygen gradients and vascular endothelial grown factor expression in an engineered 3D cell model", Cellular and Molecular Life Sciences (2008), 65(1):177-186.

Cheung; et al., "A critical review on polymer-based bio-engineered materials for scaffold development", Composites Part B: Engineering (2007), 38(3):291-300.

Karageorgiou; et al., "Porosity of 3D biomaterial scaffolds and osteogenesis", Biomaterials (2005), 26 (27):5474,5491.

Kitagawa; et al., "Three-dimensional cell seeding and growth in radial-flow perfusion bioreactor for in vitro tissue reconstruction", Biotechnology and Bioengineering (2006), 93(5):947-954.

Koch; et al., "Enhancing aniogenesis in collagen matrices by covalent incorporation of VEGF", Journal of Materials in Medicine (2006), 17(8):735-741.

Mastrogiacomo; et al., "Role of scaffold internal structure on in vivo bone formation in macroporous calcium phosphate bioceramics", Biomaterials (2006), 27(17):3230-3237.

Nomi; et al., "Principals of neovascularization for tissue engineering", Molecular Aspects of Medicine (2002), 23 (6):463-483.

Zhao; et al., "Angiogenesis, endothelial cell functions, and tumor cell growth in biodegradable and nonbiodegradable devices", Journal of Biomaterials Research—Part B Applied Biomaterials (2005), 74(2):774-781.

* cited by examiner

BIOMIMETIC CELL SCAFFOLDS

This invention relates to three dimensional implants and tissue scaffolds which promote cellular activities, such as angiogenesis, vasculogenesis, differentiation and proliferation.

Tissue hypoxia results in rapid angiogenesis in vivo, triggered by angiogenic proteins, including vascular endothelial growth factor (VEGF). Current views of tissue viability are founded on whether deeper-lying cells receive sufficient nutrients and oxygen for normal activity and ultimately survival. For intact tissues, levels of such essential nutrients are governed by micro-vascular perfusion. However, there have been few effective quantitatively defined 3D models, which enable testing of the interplay or interdependence of matrix and cell density, and path diffusion on oxygen consumption in vitro. As a result, concepts on cell vulnerability to low oxygen levels, together with the nature of cellular responses are ill defined.

The present inventors have recognised that cells in the core regions of 3-dimensional biomimetic implants do not undergo rapid cell death and may remain viable for extended periods, even under reduced oxygen conditions. Nutrient and/or metabolite gradients are generated within 3-dimensional biomimetic implants which may be useful in controlling mammalian cell growth and proliferation. These gradients may also induce the cells to produce a physiological pro-angiogenic responses. Implants producing these responses may be useful in therapeutic applications in which increased angiogenesis and/or vasculogenesis is required.

Aspects of the invention relate to the use of nutrient and/or metabolite gradients within biomimetic spatial structures to control mammalian cell growth and proliferation.

An aspect of the invention provides a scaffold for mammalian cell culture comprising:
  a gel having a pocket on the surface thereof,
    wherein the pocket contains mammalian cells.

Suitable mammalian cells include endothelial cells, fibroblasts, such as human dermal or tendon fibroblasts, stromal cells, such as bone marrow derived stromal cells and smooth muscle cells, and stem cells.

Suitable stem cells include corneal (limbal) stem cells; skin epidermal stem cells; gut (intestinal) stem cells; orogenital stem cells; bronchial and other epithelial stem cells; bone marrow stromal stem cells; and growth plate stem cells.

A pocket is a recess or crypt within the surface of the gel. The pocket comprises an opening on the surface of the gel which allows cell entry and egress and walls which define the boundaries of the pocket in the gel. Preferably, the walls of the pocket are sufficiently rigid to prevent the collapse of the pocket.

The pocket is of a suitable size to accommodate a population of mammalian cells. The dimensions of the pocket determine the number of cells within the pocket and the extent of the hypoxic gradient and may vary according to the specific application of the scaffold.

A suitable pocket may be at least 50 μm, at least 100 μm or at least 150 μm deep. A suitable pocket may be up to 500 μm deep, up to 1000 μm deep or up to 1500 μm deep.

A suitable pocket may be at least 50 μm, at least 100 μm or at least 150 μm in diameter.

In some embodiments, the pocket may be 50 μm to 2000 μm diameter, more preferably 100 μm to 500 μm in diameter and may be 100 μm to 5000 μm, preferably 200 μm to 5000 μm deep.

The walls of the scaffold may comprise additional attachment proteins, for example extracellular matrix proteins, such as fibronectin, vitronectin and fibrin.

Populations of mammalian cells, such as stem cells, within the pocket form three distinct polarities of cell-surface and cell-cell attachments which mimic natural mammalian cell niches. The mammalian cells which are adjacent to the walls of the pocket have cell-collagen contacts on one face and cell-cell contacts on the opposite face. Mammalian cells which are not adjacent the walls of the pocket (i.e. in the core of the pocket) are surrounded by other cells and have cell-cell contacts all round. Mammalian cells which are adjacent to the opening of the pocket have cell-cell contacts and cell-fluid contacts on opposing faces.

Metabolic activity of the mammalian cells located in the pocket, which may be accompanied by cell division and increasing cell density, consumes diffusible factors, nutrients, oxygen and glucose and produces waste metabolites. Since diffusible factors enter the pocket by diffusing through the gel, mammalian cells, such as stem cells, adjacent the gel are exposed to high levels of these factors. In addition, waste metabolites exit the pocket by diffusing through the gel and so these cells are exposed to low levels of cell metabolites.

Since they are surrounded by other mammalian cells consuming diffusible factors, such as oxygen, mammalian cells which are not adjacent to the gel are exposed to low levels of these factors. In addition, these cells will be exposed on all surfaces to high levels of cell metabolites.

The scaffold thus allows the generation and maintenance of concentration gradients of diffusible factors, such as nutrients, oxygen and glucose and waste metabolites, such as $CO_2$, lactate and ammonia, within the pocket which mimic natural mammalian cell niches.

The gradients of diffusible factors in the pocket stimulate the differentiation and proliferation of mammalian cells, such as stem cells, in the pocket. The differentiation and proliferation of the mammalian cells in the pocket may be controlled by modulating the concentration gradients and the polarities of the mammalian cells. This may be achieved by altering the pocket geometry, cell density, gel properties or external concentrations of factors The minimum levels of diffusible factors such as nutrients, oxygen and glucose which may be achieved within the pocket are determined by the amount of cells in the pocket. Preferably, the pocket is filled with cells only. The greater the number of cells which are seeded in the pocket, the faster this will be achieved. For example, the pocket may be seeded with greater than 5 million cells per ml, greater than 15 million cells per ml or greater than 50 million cells per ml.

As mammalian cells proliferate and the number of cells inside the pocket increases, cell migration and egress through the opening of the pocket increases. Furthermore, cells which emerge from the pocket, such as stem cells, may already be stimulated to differentiate. The rate of cell egress from the pocket is determined by the rate of proliferation and the dimensions of the pocket and the pocket opening.

A method of culturing mammalian cells may comprise
  providing a gel having a pocket on the surface thereof,
  seeding the pocket with mammalian cells, and
  incubating the gel in a culture medium;
    wherein the metabolism of the cells in the pocket causes the amount of nutrients to progressively decrease from the sides of the pocket inwards.

A suitable scaffold for control of mammalian cell growth and proliferation may be produced, for example, by plastic compression fabrication to emboss pockets onto the gel surface. Plastic compression fabrication is described in more detail in WO2006/003442

A micro-structured 'die' or template may be fabricated which corresponds to the required patterning of pockets in the gel. Contact between the die and the gel then embosses the pattern of pockets into the gel. In other words, one or more projections are present on the contact surface of the die and contact between the die and the gel causes these projections to emboss pockets in the surface of the gel. The pockets in the gel correspond in dimensions and arrangement to the dimensions and arrangement of the projections on the die and are suitable for the growth of mammalian cells. For example, a collagen gel may be plastically compressed by a die to produce crypt-like pockets 50-2000 µm diameter by 200 µm to 5000 µm deep as described above. An example of a scaffold comprising a collagen gel embossed with pockets is shown in FIG. 16.

Suitable techniques for creating projections and other micro-structure on a die or template surface are well-known in the art. For example, projections or other microstructure may be applied to glass or silicon dies by standard etching techniques or to metal dies by spark erosion techniques.

In some embodiments, a porous template or die may be employed. This allows fluid to leave the gel as it is plastically compressed, as described herein. Porous dies may be produced, for example, using sintered materials (metal, plastic or ceramic) which have been shaped to contain projections or other microstructure for embossing pockets into the gel of the scaffold.

Scaffolds for mammalian cell culture as described herein may be useful in in vivo cell growth and in biomimetic implants.

Mammalian cells which are exposed to gradients of diffusible factors, such as oxygen, within in 3D constructs may produce angiogenic factors, such as VEGF. Aspects of the invention relate to the production of angiogenic factors within an implant which may be useful in inducing or promoting angiogenesis, for example in therapeutic applications.

Gradients of angiogenic factors may be produced wholly or partially in situ after implantation. A method of inducing or promoting angiogenesis may comprise;

positioning an angiogenic implant in contact with tissue requiring vascularisation or perfusion, wherein the angiogenic implant comprises mammalian cells, and;
allowing respiration of the cells,
wherein the respiration of the cells reduces the oxygen tension in the implant, and;
the reduction in oxygen tension causing the cells to express one or more angiogenesis factors.

In some embodiments, the implant comprising the mammalian cells is cultured in vitro before positioning in contact with the tissue, such that the respiration of the cells in the in vitro culture reduces the oxygen tension in the implant, and causes the cells to express one or more angiogenesis factors, before the implant is positioned in vivo. After implantation, the cells continue to express angiogenesis factors within the host.

In other embodiments, the implant comprising the mammalian cells is not cultured in vitro before positioning in contact with the tissue.

The implant may comprise a high density bolus of mammalian cells in fluid suspension or may comprise a gel which incorporates the mammalian cells.

Gradients of angiogenic factors may be produced wholly in vitro prior to implantation. A method of inducing or promoting angiogenesis comprising;

culturing an angiogenic implant comprising mammalian cells in vitro, and;
allowing respiration of the cells such that the respiration of the cells reduces the oxygen tension, and the reduction in oxygen tension causes the cells to express one or more angiogenesis factors,
killing said mammalian cells, and,
positioning the angiogenic implant in contact with tissue requiring vascularisation or perfusion.

Oxygen tension is reduced because the supply of oxygen by perfusion from surface is exceeded by the demand for oxygen from the respiring cells. The oxygen tension within the implant may progressively decrease from the surface of the implant inwards, as the distance from the implant surface increases. This progressively decreasing in oxygen tension may cause progressively increasing amounts of angiogenesis factors to be expressed by the cells in the implant from the surface of the implant inwards i.e. as the distance from the surface increases, the oxygen tension decreases and the amount of angiogenesis factor expression increases.

The oxygen tension within the implant may progressively decrease to a minimum value at the core of implant (i.e. the part of the implant which is furthest from the surface). Alternatively, the minimum oxygen tension may occur at a part of the implant other than the core, for example when the cells are not evenly distributed through the implant.

The minimum oxygen tension in the implant is dependent on the density of cells in the implant and on the metabolic activity of the cells. Cells with high metabolic activity will generate lower oxygen tension in the implant than cells with low metabolic activity at the same density.

In some embodiments, the minimum oxygen tension within the implant is non-pathological i.e. insufficient to reduce cell viability or induce cell death. A non-pathological minimum oxygen tension may be greater than 8 mmHg (greater than 1.1 kPa or greater than 1% oxygen). For example, the oxygen tension at the core of the implant may be between 8 and 60 mmHg.

In other embodiments, the minimum oxygen tension within the implant may be pathological and cell death may occur in the implant following the production of the angiogenesis factors.

An implant comprising live mammalian cells may generate one or more angiogenesis factors in vivo, after implantation into the host. The cells in the implant produce one or more angiogenesis factors in response to reduced oxygen tension in the implant after implantation. The one or more angiogenesis factors expressed by the cells diffuse into the tissue adjacent the implant and induce or promote angiogenesis in the tissue. The production of a physiological combination of angiogenesis factors at physiological concentrations by the cells leads to the stimulation of a physiological angiogenic response in the tissue, leading to increased vascularisation of the tissue.

An implant may generate the one or more angiogenesis factors in vitro, before implantation into the host. The cells in the implant produce one or more angiogenesis factors in response to reduced oxygen tension in the implant during in vitro culture in a standard culture medium. Suitable conditions for the culture of mammalian cells are well known in the art. In some circumstances, it may be desirable to reduce the oxygen supply to the in vitro culture to increase or accelerate the reduction in oxygen tension (i.e. the onset of hypoxia) within the implant. As the oxygen tension reduces within the implant, the one or more angiogenesis factors expressed by the cells diffuse into the implant adjacent the cells. Following in vitro preconditioning, the implant comprising the mammalian cells may then be implanted in vivo, such that the cells continue to express the one or more angiogenic factors within the host. Alternatively, the mammalian cells in the implant may be killed after in vitro culture, for example by freezing. The implant may then be stored before implantation. After implantation, the one or more angiogenesis factors which were expressed in the implant during the in vitro culture diffuse into the tissue adjacent the implant and induce or promote angiogenesis in the tissue.

The diffusion of a physiological combination of angiogenesis factors at physiological concentrations from the implants described herein leads to the stimulation of a physiological angiogenic response in the surrounding tissue, leading to increased vascularisation of the tissue.

The physiological angiogenic response may be directional. For example, the production of a concentration gradient of angiogenesis factors promotes angiogenesis up the concentration gradient (e.g. towards the core of the implant).

The angiogenesis factors expressed by cells in the angiogenic implant may also facilitate the differentiation of endothelial cells. Suitable endothelial cells may be incorporated the angiogenic implant or may be positioned adjacent the implant.

An angiogenic implant as described herein may be useful in promoting angiogenesis and attracting blood vessels to a tissue or construct requiring vascularisation or perfusion, for example a native tissue, graft, autograph, transplant or tissue equivalent construct.

Angiogenic implants as described herein provide a source of angiogenesis promoting factors and form a focal point within a tissue or construct for angiogenesis. Angiogenic implants may be positioned at any site at which increased vascularisation or perfusion is required and have a wide range of therapeutic applications.

Angiogenic implants may be useful, for example in promoting vascularisation in large (mm scale) tissue engineered constructs; clinical grafts (e.g. skin or tendon grafts), native autographs, transplants, wound sites; hormone implants; non-union fractures; and sites of myocardial infarction.

Angiogenic implants may be useful, for example in promoting perfusion, for example in slow release drug depots; wound sites; hormone implants; non-union fractures; and sites of myocardial infarction.

In the methods described herein, an implant may be positioned within or in contact with a native tissue, preferably at a region requiring vascularisation or perfusion. If required, the implant may be fixed in position by any convenient technique. For example, it may be sutured or glued in place. In some embodiments, a high density bolus of cells in fluid suspension may be injected at a suitable deep tissue point to form a localised depot. Suitable deep tissue points may include tissue pockets and between layers of tissue.

After positioning an implant containing mammalian cells within a host, the cells in the implant respire and consume oxygen. This decreases oxygen tension within the angiogenic implant and causes the cells to express one or more angiogenesis factors.

Whether expressed before or after implantation, the angiogenesis factors within the implant diffuse from the implant into the adjacent tissue or tissue equivalent construct, promoting angiogenesis in the native tissue. Native tissue requiring vascularisation or perfusion may include failed repair sites, chronic wounds, non-union fracture sites, and myocardial infarct sites or sites needing enhanced drug or hormone dosing.

In the methods described herein, an angiogenic implant may be positioned within an outer implant. After positioning, the cells in the angiogenic implant respire and consume oxygen. As described above, this leads to the production and diffusion of angiogenesis factors from the angiogenic implant into the outer implant, promoting angiogenesis in the outer implant. Outer implants may be natural or engineered implants, tissue equivalent constructs, reconstruction or cosmetic grafts and transplants. In some embodiments, the outer implant may be an acellular collagen gel.

Other aspects of the invention relate to angiogenic implants comprising mammalian cells which may be useful in methods of promoting angiogenesis as described herein.

An angiogenic implant comprising mammalian cells as described herein may be used in a method of promoting angiogenesis comprising;
   positioning an angiogenic implant in contact with tissue requiring vascularisation or perfusion, wherein the angiogenic implant comprises mammalian cells, and;
   allowing respiration of the cells,
   wherein the respiration of the cells reduces the oxygen tension, and;
   the reduction in oxygen tension causing the cells to express one or more angiogenesis factors.

An angiogenic implant comprising mammalian cells as described herein may be used in the manufacture of a medicament for use in method of promoting angiogenesis comprising;
   positioning an angiogenic implant in contact with tissue requiring vascularisation or perfusion, wherein the angiogenic implant comprises mammalian cells, and;
   allowing respiration of the cells,
   wherein the respiration of the cells reduces the oxygen tension, and;
   the reduction in oxygen tension causing the cells to express one or more angiogenesis factors.

Suitable methods of promoting angiogenesis are described in more detail above.

Other aspects of the invention relate to angiogenic implants comprising one or more angiogenesis factors which may be useful in methods of promoting angiogenesis as described herein.

An angiogenic implant may be produced by a method which comprises;
   culturing an implant comprising mammalian cells in vitro;
   allowing respiration of the cells such that the respiration of the cells reduces the oxygen tension, and the reduction in oxygen tension causes the cells to express one or more angiogenesis factors, and;
   killing said mammalian cells.

After expression of the one or more angiogenesis factors, the implant may be treated to kill the mammalian cells therein. Any convenient method may be employed. In some embodiments, the implant may be frozen, for example by immersion in liquid nitrogen.

Once the mammalian cells have been killed, the implant may be stored prior to implantation. Conveniently, the implant may be stored at 4° C., −20° C. or −70° C. in accordance with routine techniques.

An angiogenic implant comprising one or more angiogenesis factors may be used in a method of promoting angiogenesis comprising;
   positioning the angiogenic implant in contact with tissue requiring vascularisation or perfusion, wherein the angiogenic implant comprises one or more angiogenesis factors, and;
   allowing said one or more angiogenesis factors to diffuse from the implant to the tissue.

An angiogenic implant comprising one or more angiogenesis factors may be used in the manufacture of a medicament for use in method of promoting angiogenesis comprising;

positioning the angiogenic implant in contact with tissue requiring vascularisation or perfusion, wherein the angiogenic implant comprises one or more angiogenesis factors, and;

allowing said one or more angiogenesis factors to diffuse from the implant to the tissue.

Angiogenesis factors include proteins such as chemokines and cytokines which stimulate or promote the formation, development and growth of new blood vessels in a tissue. The one or more angiogenesis factors expressed by the cells in the angiogenic implant may include one or more of acidic and basic fibroblast growth factor (FGF), transforming growth factor alpha (TGF-alpha) and beta (TGF-beta), tumor necrosis factor (TNF), platelet-derived growth factor (PDGF), vascular endothelial cell growth factor (VEGF), HIF-1a and angiogenin. In some embodiments, the one or more angiogenesis factors may include VEGF.

Suitable gels for use in the implants and scaffolds described herein may comprise a matrix of scaffold fibres and an interstitial fluid. Gels are formed by the coalescence and elongation of scaffold fibrils, as the fibrils form a continuous network around the aqueous interstitial liquid which originally held the monomers. For example, triple helical collagen monomers may be initially dissolved in dilute acid and then induced to polymerise (aggregate) to fibrils (e.g. at 37° and neutral pH). As the fibrils polymerise, there is a phase change and the solid network of fibrils 'supports' the remaining interstitial liquid in approximately the same volume and shape—i.e. it gels. Phase transition from soluble monomer to solid polymer is characteristic of a gel.

Any hydrated polymer material may be suitable for use in the gels described herein, including naturally occurring polymers, for example proteins, such as silk, fibrin, fibronectin, elastin or collagen (e.g. collagen type I), glycoproteins such as fibronectin, or polysaccharides such as chitin, or cellulose. In some preferred embodiments, the matrix fibres are made collagen. Native fibril forming collagen types are preferred including collagen types are I, II, III, V, VI, IX and XI and combinations of these (e.g. I, III V or II, IX, XI). For example, collagen type I may be used as the gel or scaffold material. In some preferred embodiments, the gel may comprise 5 to 25% collagen type I (dry/wet weight ratio), more preferably about 10%. In some preferred embodiments, the gel may comprise 15 to 20% collagen type I (dry/wet weight ratio), more preferably about 10%.

Other suitable fibrous scaffold materials include synthetic polymers i.e. polymers that are not naturally present in the human or animal body. Suitable polymers include organic polymers such as polylactone, polyglycone and polycaprylolactone, inorganic polymers such as phosphate glass and synthetic, gelling polypeptide gels.

In some embodiments, the fibrous scaffold material may be a composite material comprising two or more different types of fibre. For example, the scaffold may comprise fibronectin and collagen, collagen and polylactide, fibrin and collagen, collagen fibres and carbon-nanotubes, or fibrin, collagen and fibronectin.

The interstitial liquid is typically an aqueous liquid which supports the growth and proliferation of the cells contained in the gel. Suitable liquids include mammalian cell culture media such as Eagles MEM solution. Techniques for formulating and casting gels for use as biomaterials are well-known in the art (see, for example, WO2006/003442; WO2007/060459; Marenzana et al 2006 Exp Cell Res 312 423-433; Tomasek et al (2002) Nat Rev Mol Cell Biol 3 349-363; Harris et al Nature 290 (1981) 249-251; Elsdale et al 1972 J Cell Biol. 54 626-637; Kolodney et al J Cell Biol. (1992) 117 73-82; Eastwood et al Biochem Biophys Acta 1201 (1994) 186-192).

In general, high density gels are preferred to facilitate the generation of gradients of diffusible factors, such as oxygen.

A suitable gel for use in the implants described herein may have a liquid phase of >70% (wet/dry weight ratio), >75%, >80%, >85%, or >90%. For example, a suitable gel may have a liquid phase of 75% (wet/dry weight ratio) to 95%, typically about 88%.

A suitable gel described herein may have a may have an oxygen diffusion coefficient of 1 to $10 \times 10^{-6}$ $cm^2/s^-$, more preferably 4 to $5 \times 10^{-6}$ $cm^2/s^{-1}$.

Gel permeability may also be measured by determining the $O_2$ re-equilibrium rate after depletion, for example using sodium sulfite or $N_2$ saturation. In some embodiments, the gel may have an $O_2$ re-equilibrium rate over a 1 mm shortest diffusion path of 2 to 4 mmHg/min, preferably about 3 mmHg/min in an air saturated solution, following $O_2$ depletion.

The permeability of a gel suitable for use in an implant may be equivalent to a gel containing 5% to 25% collagen, preferably about 10% collagen (dry/wet weight ratio). In some embodiments, a dense gel may be used which has a permeability equivalent to a gel containing 15% to 20% collagen.

The gel may be uniform throughout the implant and the angiogenic factors produced by the cell may diffuse through the gel uniformly in all directions.

Alternatively, the gel may be structured such that the angiogenic factors produced by the cell diffuse more quickly through the gel in specific directions and provide directional gradients of angiogenic factors i.e. gradients in specific directions away from the producer cells. For example, the gel may comprise multiple layers. Diffusion of the angiogenic factors may be quicker between the gel layers than through the gel layers, providing a directional gradient of angiogenic factors.

For example, a gel comprising multiple layers may be formed by rolling up a flat gel into a cylindrical implant (i.e. a cylinder having a cross-section). The speed of diffusion of the angiogenic factor through the gel will be slow in a radial direction across the layers of gel (i.e. perpendicular to the spiral axis) and fast in a longitudinal direction between the layers of gel (i.e. parallel to the spiral axis).

This vectored diffusion may be useful in promoting angiogenesis in tissues in which directional vascularisation is important, such as tendon, nerve, skin and bone.

In the methods of promoting angiogenesis described herein, the gel incorporates viable mammalian cells, preferably human cells. The minimum oxygen tension which may be achieved within the gel is determined by the density of the cells in the gel. Preferably, the density of cells within the gel is sufficient to reduce $O_2$ levels to less than 60 mmHg, less than 50 mmHg, less than 40 mmHg, less than 30 mmHg, less than 20 mmHg less than 10 mmHg, less than 5 mmHg or less than 1 mmHg. The density of cells within the gel may be sufficient to reduce $O_2$ levels to between 8 and 60 mmHg, preferably between 20 and 60 mmHg. For example, the gel may be seeded with greater than 12 million cells per ml, greater than 15 million cells per ml or greater than 20 million cells per ml.

In some embodiments, the cells are fibroblasts, such as human dermal or tendon fibroblasts.

In addition to producing an extracellular matrix, fibroblasts are able to tolerate low oxygen tensions and have a low metabolic rate and therefore a low oxygen demand, relative to other cell types. As a result, oxygen tension may be reduced by fibroblast respiration more slowly than other cell-types. Furthermore, the production of angiogenesis factors may also reduced or delayed in implants incorporating fibroblasts, relative to implants incorporating other cell-types.

In some preferred embodiments, the cells for use in angiogenic implants are not fibroblasts. Preferred cells may have high metabolic activity and therefore generate gradients rapidly or may be sensitive to low $O_2$, and so produce angiogenic factors rapidly, relative to fibroblasts. Suitable cells may be selected from the group consisting of stromal cells, such as bone marrow derived stromal cells, smooth muscle cells and stem cells, such as corneal (limbal) stem cells, skin epidermal stem cells, gut (intestinal) stem cells, orogenital stem cells, bronchial and other epithelial stem cells, bone marrow stem cells, growth plate stem cells. Increased metabolic activity reduces the time for the generation of hypoxia and production of angiogenic factors.

In some preferred embodiments, suitable cells include allogeneic GMP produced cells (e.g. human neonatal fibroblasts), allogeneic or autologous blood cells, or allogeneic or autologous stromal stem/progenitor cells from bone marrow or other sources, all of which are available for clinical use at GMP grade.

The type of cell may reflect the tissue or application for which the angiogenic implant is to be used.

Suitable cells may include allergenic waste human cells, such as time expired marrow cells or blood cells; pre-cultured fibroblast cells; and animal cells, for example humanised cells from transgenic pigs or sheep.

The cells may be derived from the same tissue as the vascularised tissue or may be derived from a different tissue to the vascularised tissue.

The results set out herein show that cells may remain viable in the core region of angiogenic implants over extended periods. For example, in some embodiments, after 24 hours in situ, cell viability may be at least 80%, at least 90% or at least 95% at the core of the implant. After 5 days in situ, cell viability may be at least 70%, at least 65% or at least 80% at the core of the implant and at least 80%, at least 90% or at least 95% at the surface of the implant.

In other embodiments, the cells do not remain viable but produce the one or more angiogenic factors before cell death occurs. As described above, in some embodiments, the angiogenic implant may be treated to kill the cells following production of the one or more angiogenic factors.

Cells may be seeded within the matrix by mixing them with the liquid scaffold matrix and then allowing the liquid matrix to solidify into a gel. Seeding of the matrix is preferably performed under suitable conditions of temperature, pH, ionic strength and sheer to maintain viability, prior to gel formation. The initial cell density in the gel may be from about $1 \times 10^4$ to $1 \times 10^7$ cells per ml, more preferably from about $5 \times 10^5$ to $1 \times 10^6$ cells per ml.

In some embodiments, the angiogenic implants or mammalian cell scaffolds as described herein may be produced by a method comprising plastically compacting a gel which is seeded with cells. This increases the density of cells within the gel. Plastic compaction involves deforming an object such as a gel to reduce its volume, such that the object substantially retains its new volume, even after the cause of compaction is removed. Plastic compaction is a rapid, cell-independent process which results from subjecting the gel to a physical treatment, such as an external force or pressure, which expels interstitial liquid from the gel, such that it does not return on removal of the load: i.e. the gel undergoes a plastic compaction.

For example, plastic compaction may form a sheet comprising cells, which may be rolled or folded to produce a multilayer implant. Plastic compaction of gels, including gels seeded with cells, is described in more detail in WO2006/003442.

Plastic compaction may improve the mechanical properties of the gel. Unconfined compaction of a gel expels interstitial liquid, which does not return on removal of the load: i.e. the gel undergoes a plastic compaction. In an untreated gel, the scaffold matrix is generally in a gross, hydrated form. This scaffold structure collapses during plastic compaction without loss of structural detail, dehydrating the scaffold in the gel, and leading to increased density and strength.

The plastic compaction process may be optimised to achieve the desired final ratio of fibres and cells from a standard starting gel. A standard gel, for example, may comprise 1 to 4% collagen and 0.2 to $10 \times 10^6$ cells per ml.

The gel environment is preferably maintained at physiological conditions (e.g. temperature, pH, hydration and ionic strength) for the cells to survive. It is preferred that plastic compaction does not alter the ionic properties of the gel fluid significantly from physiological conditions.

Following compaction, the gel may be subjected to repeated cycles of uniaxial tensile loading to improve its mechanical properties. Suitable cycling is described in WO2007/060459. In a compacted collagen gel, repetitive cycles of loading increase the fusion of collagen fibrils to produce a biomaterial which has improved material strength (i.e. increased break stress, break strain and/or elastic modulus).

Additional processing of the gel or biomaterial may be performed to produce a tissue equivalent implant for the promotion of angiogenesis. The gel or biomaterial may, for example, be moulded and/or shaped to produce a tissue equivalent implant. For the gel or biomaterial may be moulded into a predetermined shape and/or may be subjected to plastic compaction which may be symmetrical or asymmetrical.

The gel or biomaterial comprising the cells may be shaped, cut or moulded into any convenient implant form, for example, a patch, block, tube, tape, strip, ring, toroid, capillary, roll, sheet or thread. The final shape of the tissue equivalent implant will depend on the particular context in which it is to be used. In some embodiments, the tissue equivalent implant may have a pliable form which is suitable for further shaping.

The time between implantation and production of angiogenic factors is dependent on the cell density, path length and cell metabolic activity of the implant. The properties of an angiogenic implant may be optimised for a specific application, site or tissue by altering these parameters. As described above, the implant may be pre-conditioned in vitro in order to produce angiogenic factors before implantation. This may be useful, for example, if the implant is seeded with low numbers of cells (e.g. $2 \times 10^7$ cells per ml or less, $1 \times 10^7$ cells per ml or less, or $5 \times 10^6$ cells per ml or less)

Once formed, an implant comprising cells as described herein will be steadily filled with angiogenic factors in the appropriate proportions and ratios to stimulate a physiological angiogenic response in adjacent tissue.

In some embodiments, the implant comprising viable mammalian cells may be used either directly or after pre-conditioning in vitro as an angiogenic motor.

In other embodiments, after in vitro culture, the implant may be frozen or freeze-dried either whole or with subsequent sectioning or other controlled fragmentation and/or partitioning. Although no longer containing viable cells, the resultant implant comprises angiogenic factors which diffuse out of the implant to promote angiogenesis in surrounding tissue. The direction of diffusion may be controlled by the structure (nano-micro-scale) of the original gel matrix.

Implants comprising angiogenic factors without viable cells will be highly stable with a long shelf life and may be useful for off-the-shelf use in clinical or veterinary applications for stimulating angiogenesis. An implant may, for example, be delivered directly during surgery to any clinically required location; injected using conventional needles or administered as part of other treatments using conventional endoscopes. This allows the control of local tissue perfusion by the clinician.

The methods described herein may be useful in promoting angiogenesis in tissue requiring vascularisation or perfusion, for example tissue with deficient vascularisation. Tissue with deficient vascularisation may include any tissue that would benefit from stimulation of angiogenesis, increased blood flow, and/or increased vascularity.

For example, the methods described herein may be useful in promoting angiogenesis to accelerate or enhance the healing of wounds or ulcers, the vascularization of skin grafts, musculocutaneous flaps or other surgically transplanted tissue (e.g. reattached limbs) so as to preserve their function and viability; the healing of surgically created anastomoses (for example, in re-connecting portions of the bowel after gastrointestinal surgery) or to improve the growth of skin.

The methods described herein may also be useful in promoting angiogenesis in the treatment of diseases and conditions associated with reduced or impaired vascularisation or diseases and conditions that would benefit from the stimulation of angiogenesis, increased blood flow, and/or increased vascularity. Examples of conditions which may be treated include any condition associated with an obstruction of a blood vessel, such as an artery, vein, or capillary. Examples of conditions include vascular occlusive diseases, such as coronary occlusive disease, carotid occlusive disease and arterial occlusive disease; peripheral arterial disease; atherosclerosis; myointimal hyperplasia (e.g., due to vascular surgery or balloon angioplasty or vascular stenting); thromboangiitis obliterans; thrombotic disorders; mesenteric or limb ischemia; stenosis; vasculitis, myocardial and cerebral infarctions or other vascular death, stroke, loss of limbs associated with decreased blood flow.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures and tables described below.

Figure 4:
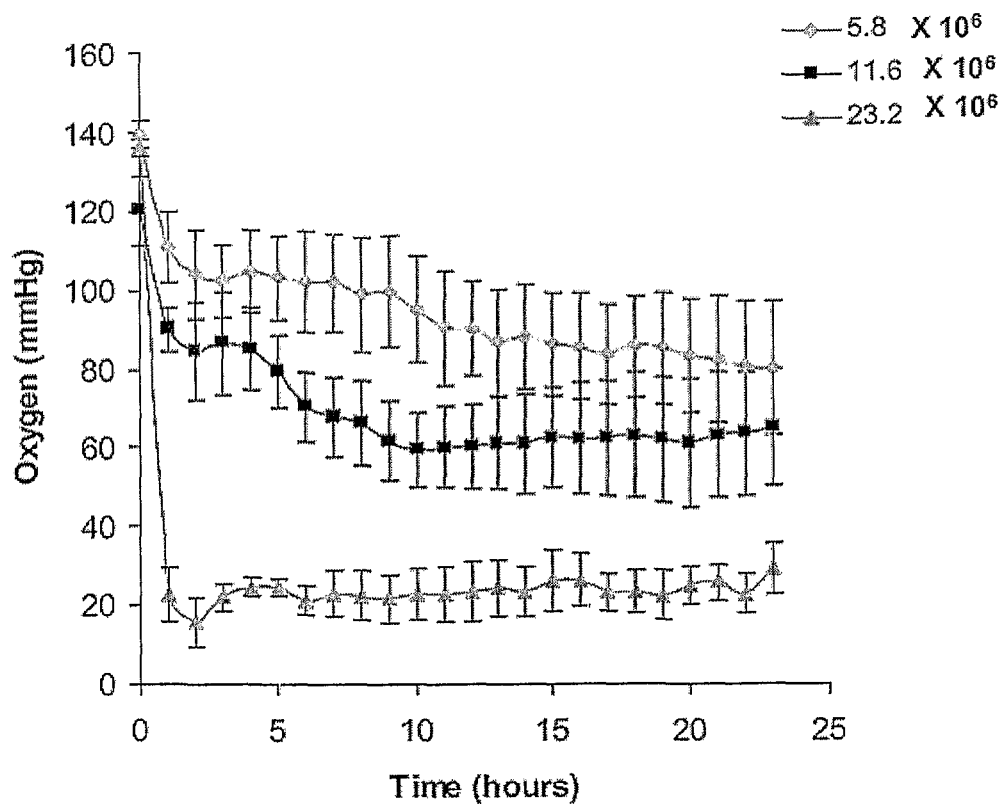

FIG. 4 shows oxygen levels in the centre of cell-seeded plastic compression constructs. Oxygen levels at different cell densities were measured, $5.8 \times 10^6$-$23.2 \times 10^6$ cells/ml, magnification bar 50 mm ($0.5 \times 10^6$-$2 \times 10^6$ cells/construct), * p<0.0001. Average of n=3 for each data set is presented here. Time 'zero' is taken as the time point when the probe was positioned in the construct.

Figure 5:
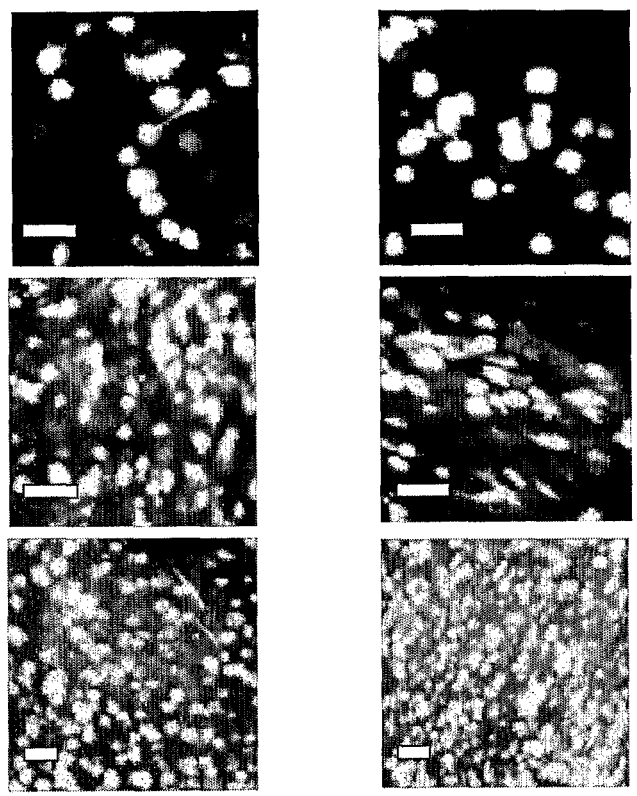

FIG. 5 shows confocal images of the central and outer region of the plastic compression constructs seeded with $5.8 \times 10^6$ (top), $11.6 \times 10^6$ (middle) and $23.2 \times 10^6$ cells/ml (bottom).

Figure 6:
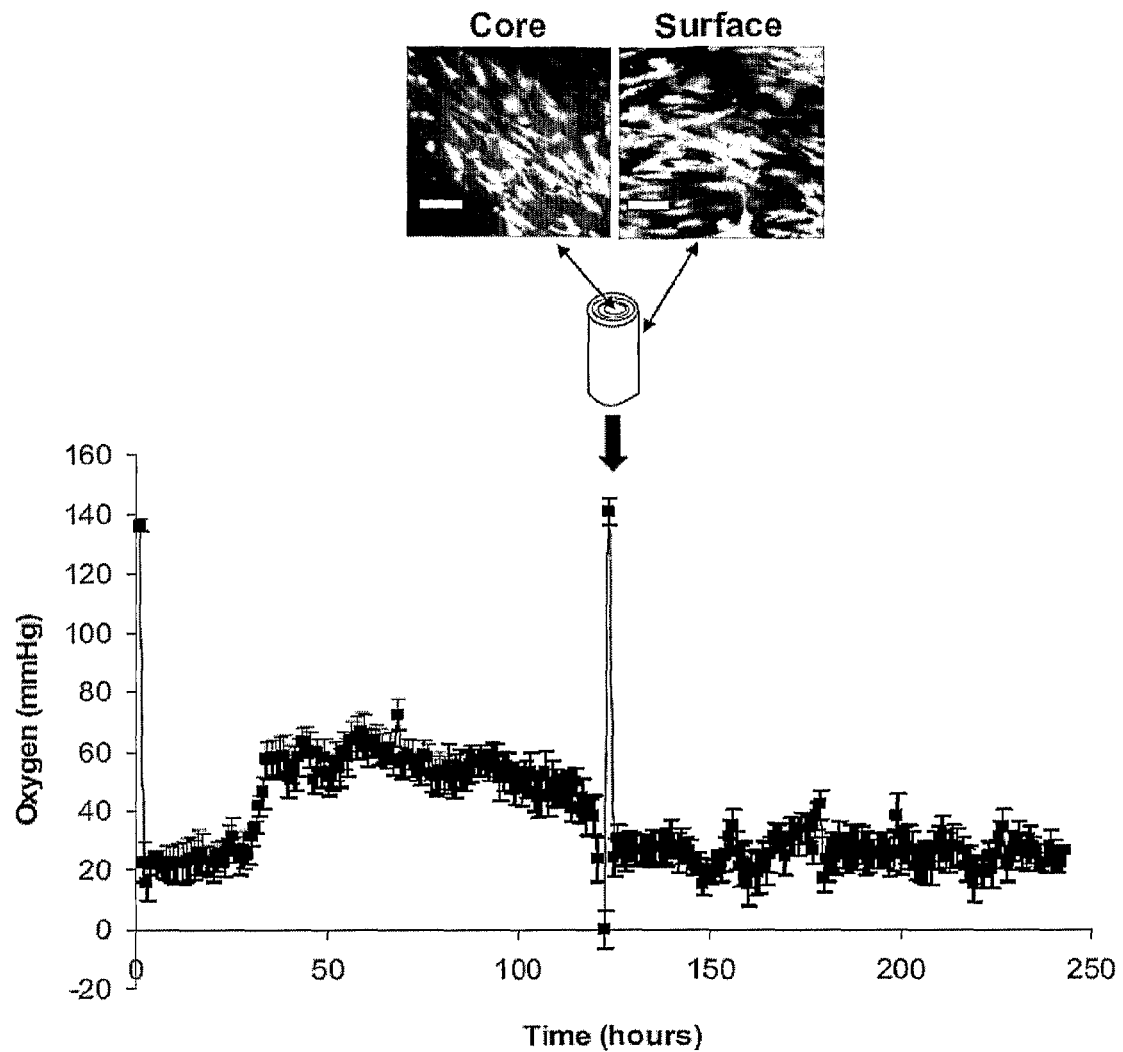

FIG. 6 shows oxygen levels in the centre of a cell-seeded construct, $2 \times 10^6$ cells in a construct ($23.2 \times 10^6$ cells/ml), over a 10-day period, with supporting cell viability on day 5 from the centre and surface of the construct. Graph represents a mean of n=3. Magnification bar 100 mm for micrographs.

Figure 7:
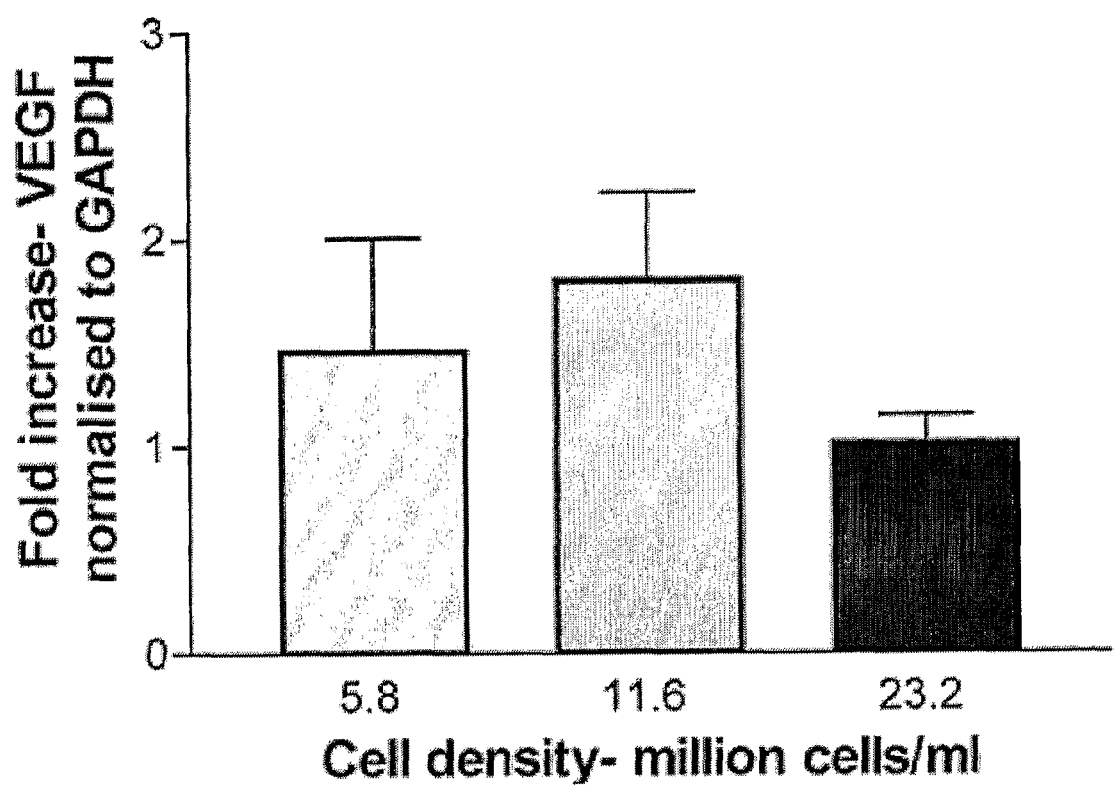

FIG. 7 shows VEGF levels in constructs of varying cell density at 24 h. No significant difference was found in VEGF levels between different cell densities.

Figure 8:
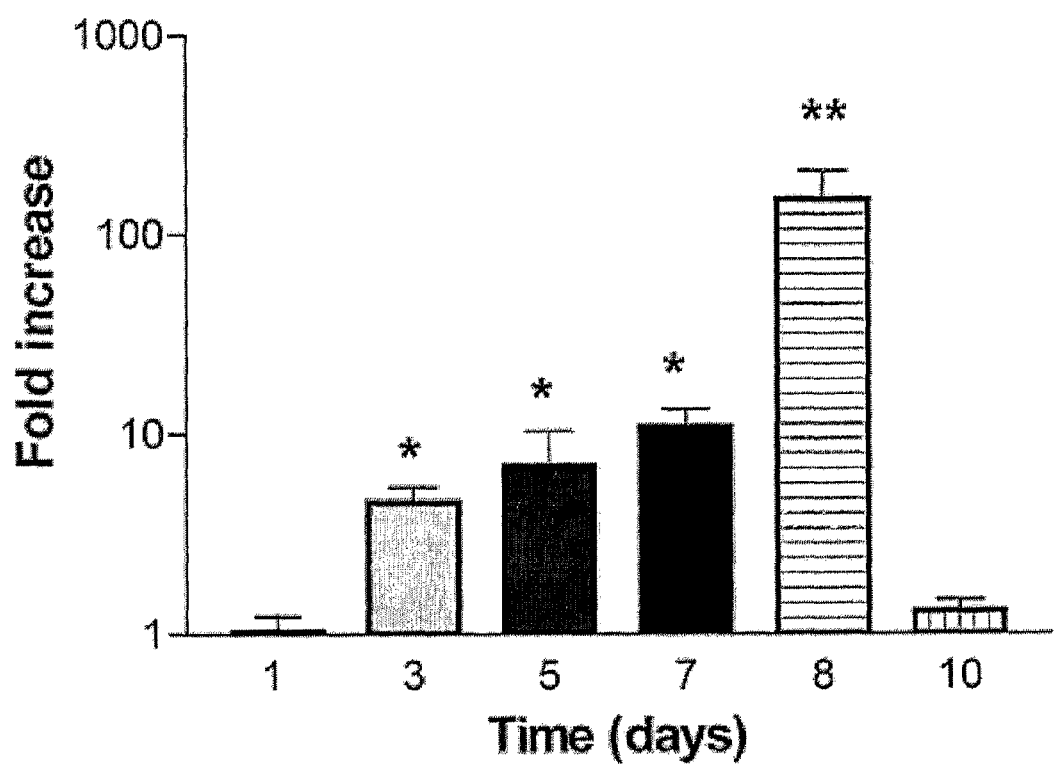

FIG. 8 shows the level of VEGF in constructs containing 2 million cells/construct over a 10-day period (normalised to GAPDH, with day 1 as the set calibrator) shows a statistically significant increase measured on day 8, which then dropped by day 10 (** p<0.001, * p<0.05).

Figure 9:
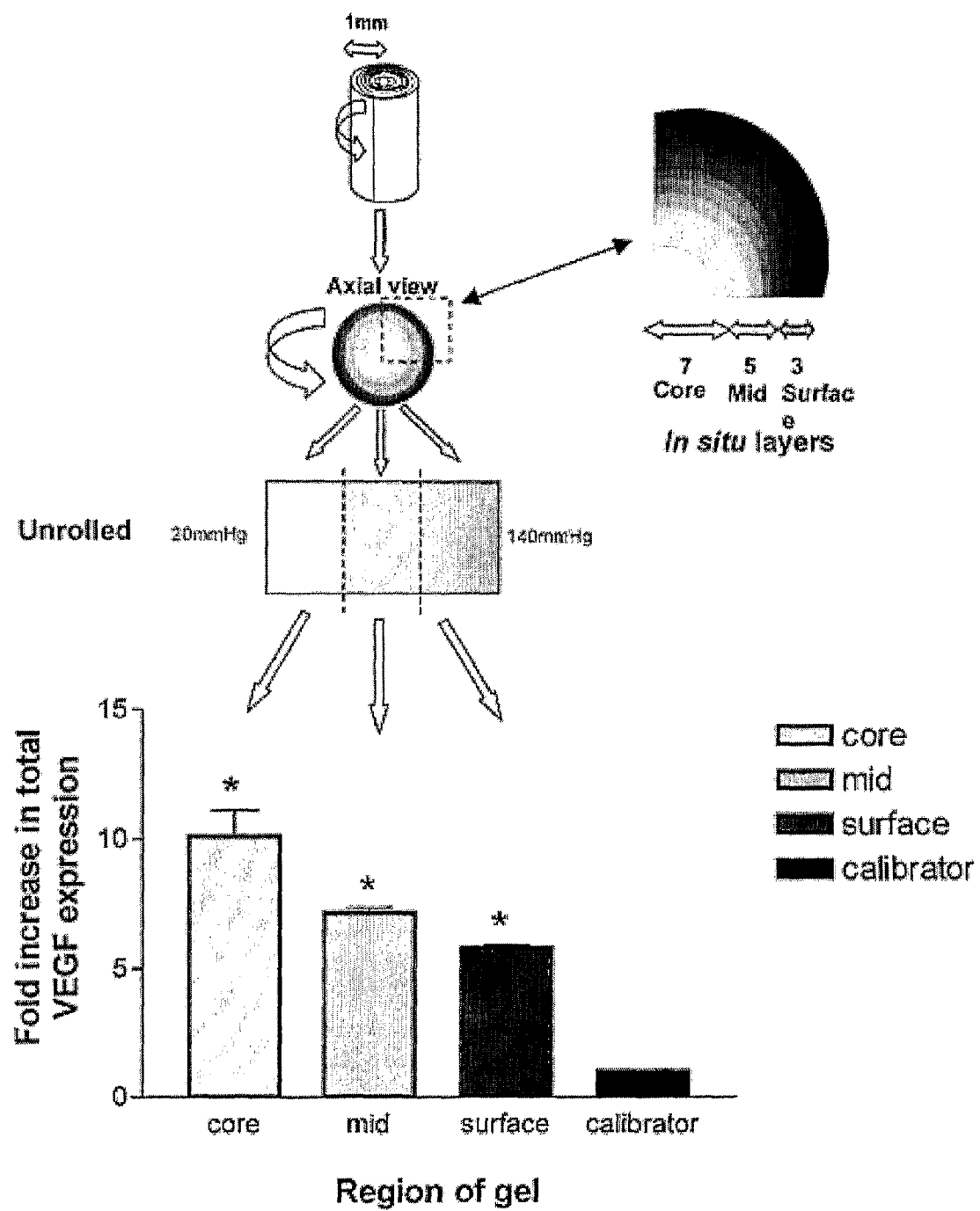

FIG. 9 shows spiral constructs seeded with $2 \times 10^6$ cells, cultured for 8 days (peak in VEGF expression) and unrolled to study VEGF in three regions of the construct (because of spiralling these regions corresponded to three unequal thicknesses of the original construct core, mid and surface, approximately 7, 5 and 3 layers respectively). VEGF expression was normalised to GAPDH, with day 1 as the set calibrator, which was $23.2 \times 10^6$ cells/ml at 24 h. There were significantly higher levels of VEGF found in the centre of the gels (* p<0.001).

Figure 10:
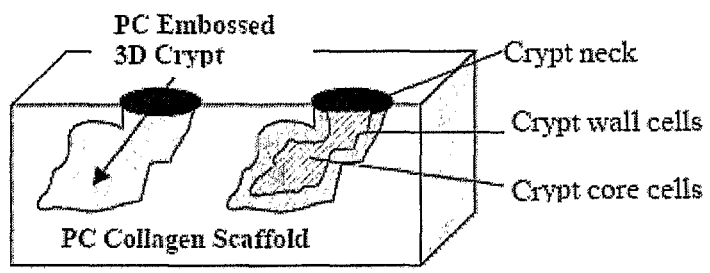

FIG. 10 shows an example of a biomimetic stem cell niche as described herein.

Figure 11:
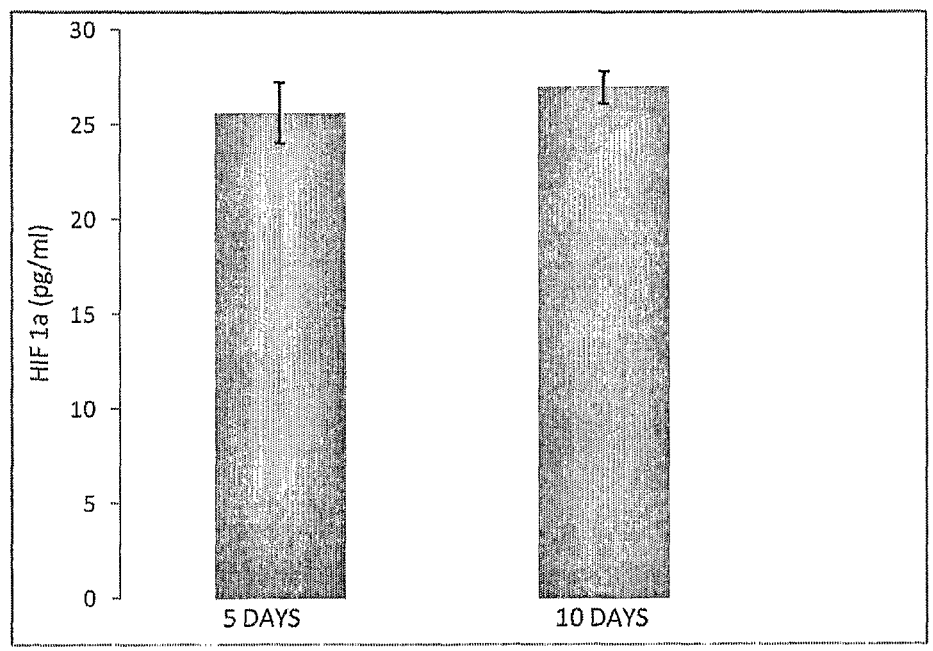

FIG. 11 shows levels of HIF-1a determined by ELISA in a collagen construct seeded with $2 \times 10^6$ HDFs and incubated for 5 and 10 days in vitro.

Figure 12:
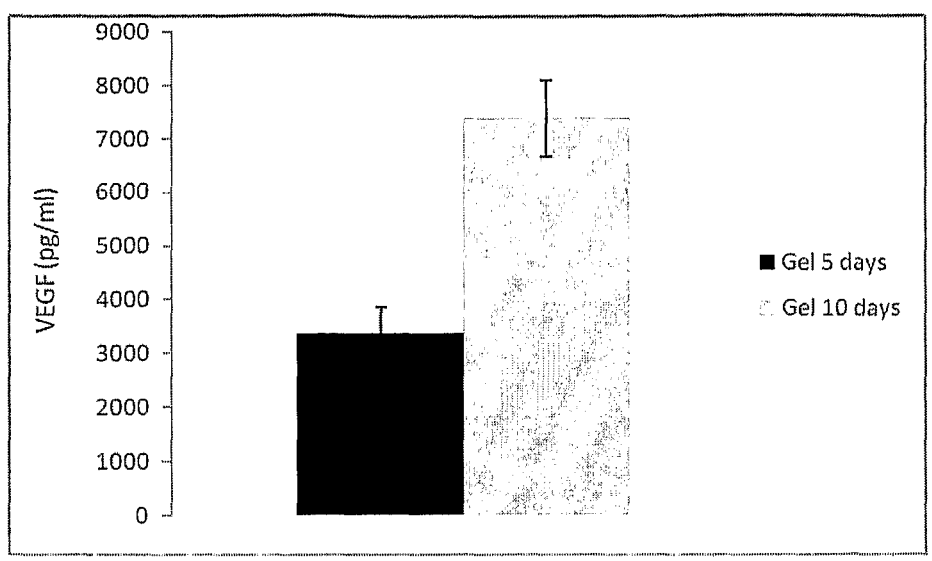

FIG. 12 shows levels of VEGF determined by ELISA in a collagen construct seeded with $2 \times 10^6$ HDFs and incubated for 5 and 10 days in vitro.

Figure 13:
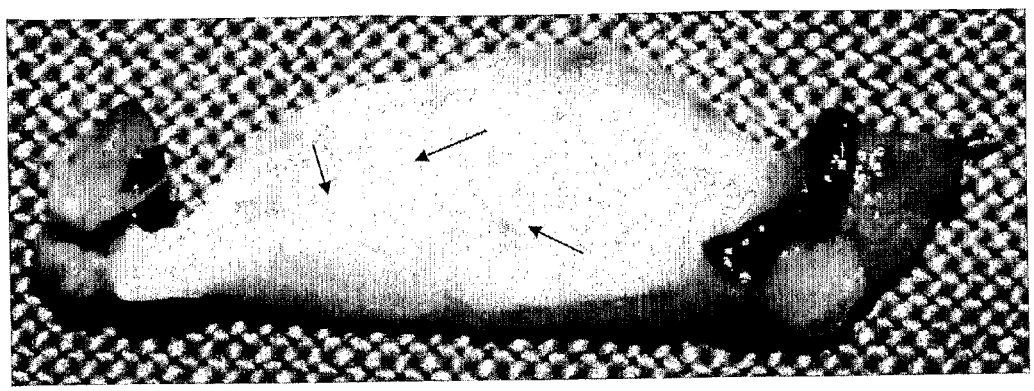
Figure 13:
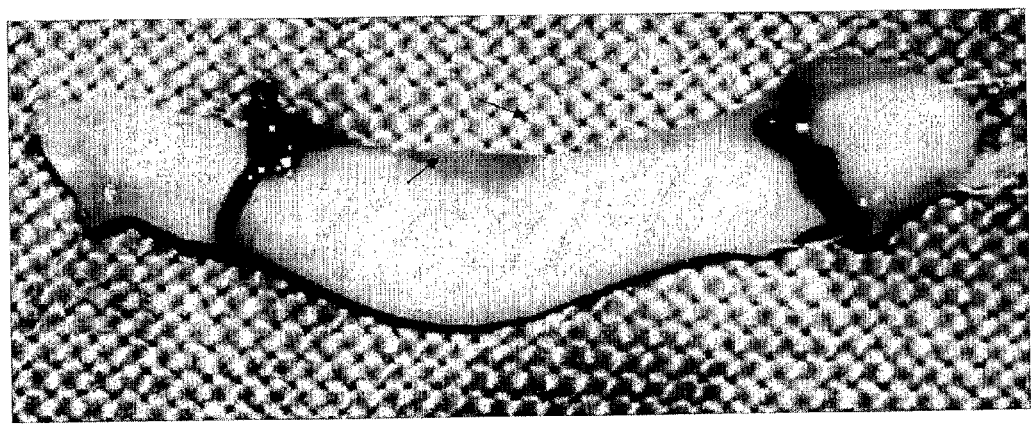

FIG. 13 shows collagen constructs seeded with $2 \times 10^6$ HDFs, preconditioned by incubation for 5 days in vitro (top) or without preconditioning (bottom) and implanted subcutaneously into a rabbit for 1 week.

Figure 14:
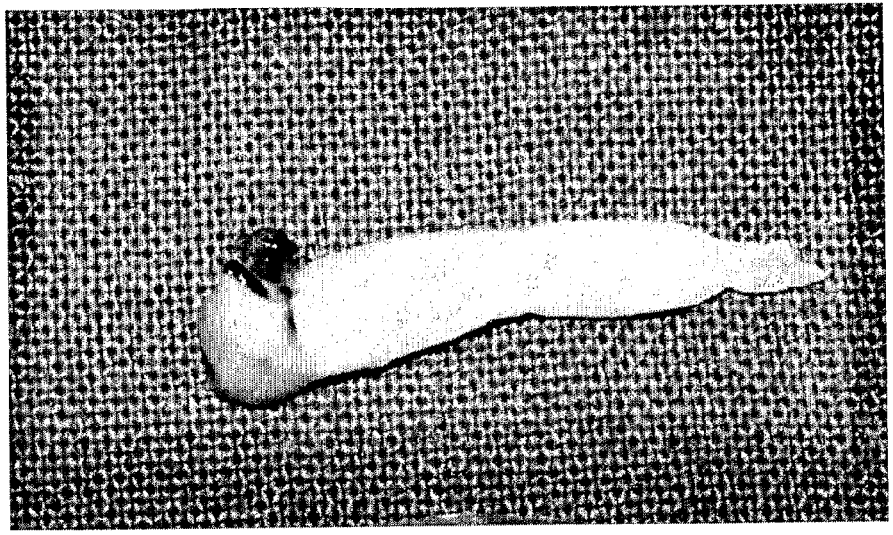
Figure 14:
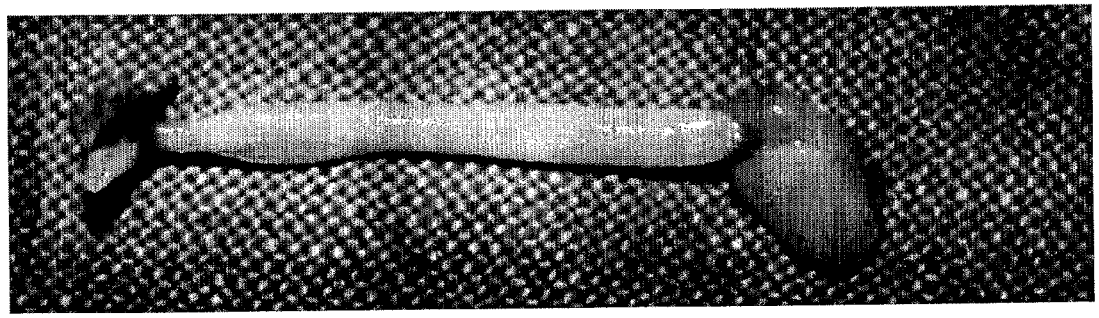

FIG. 14 shows (top panel) a control collagen construct which has been seeded with $2 \times 10^6$ HDFs, frozen in liquid nitrogen without preconditioning and implanted subcutaneously into a rabbit for 1 week and (bottom panel) a control acellular collagen construct after subcutaneous implantation in a rabbit for 1 week, without seeding with cells or freezing.

Figure 15:
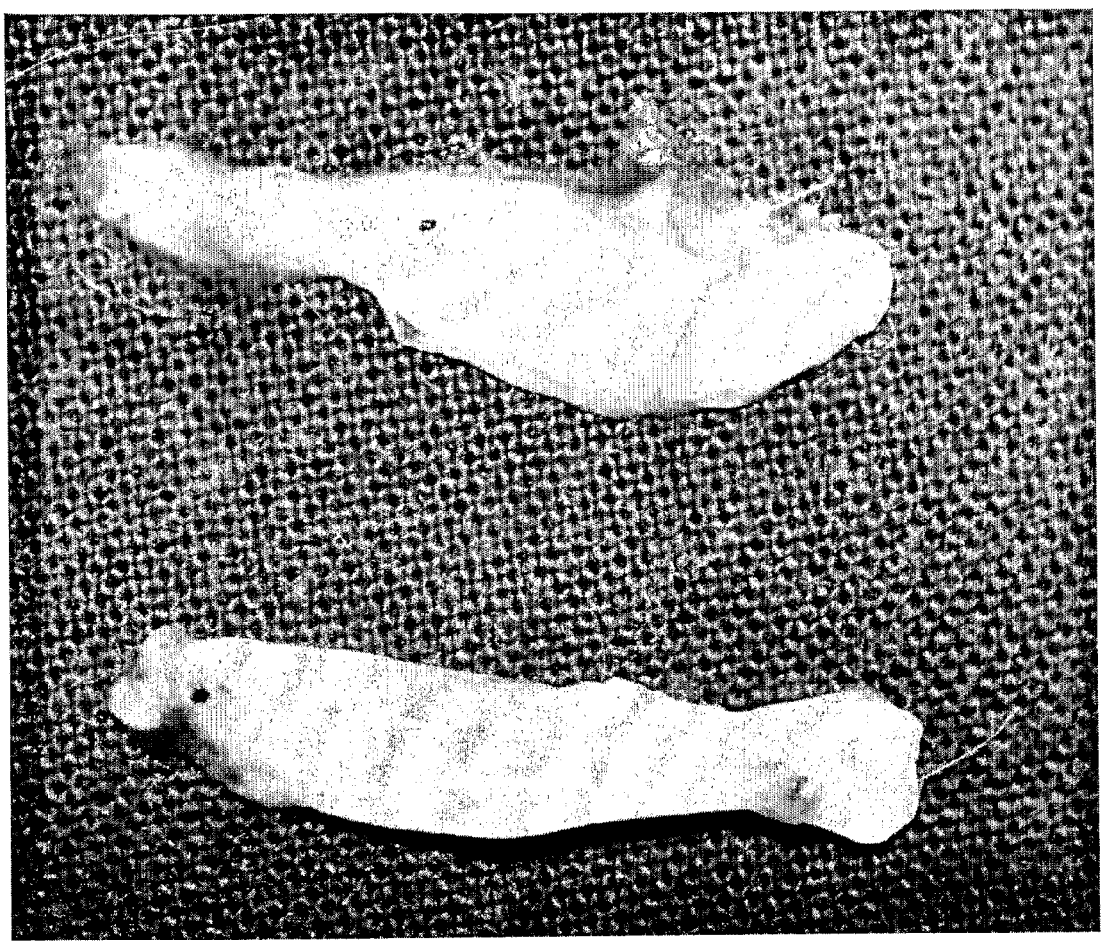

FIG. 15 shows collagen constructs seeded with $2 \times 10^6$ HDFs and preconditioned by incubation for 10 days in vitro, and then frozen in liquid nitrogen and then implanted subcutaneously into a rabbit for 1 week.

Figure 16:

FIG. 16 shows a collagen scaffold with embossed pockets for accommodating mammalian cells.

Methods

Cell Culture and Expansion.

Human dermal neonatal fibroblasts were explanted from neonatal foreskins (obtained freshly from the operating theatre, with full ethical approval, following surgery for circumcision), as previously described [13]. Cells were maintained in Dulbecco's modified Eagles medium(DMEM, Gibco, Paisley, UK), supplemented with 10% FCS (First Link, West Midlands, UK), 2 mM glutamine and penicillin/streptomycin (1000 U/ml; 100 mg/ml, Gibco Chemicals). For removal of cells from monolayer culture, flasks containing cells were washed with 0.1 M PBS, and incubated with trypsin (0.5% in 5 mM EDTA) for 5 min at 37 8 C.

3D Plastic Compressed Collagen Gel Culture

Once detached, cells were counted and embedded in 3D collagen type I gels. Collagen gels were set in a mould (2.2× 3.3×1 $cm^3$). For collagen gel preparation, 0.5 ml 10_ Eagles MEM solution (Gibco) was added to 4 ml rat-tail type I collagen (First Link) in 0.1 M acetic acid, protein concentration 2.035 mg/ml, neutralized with 5 M NaOH, using the indicator colour changes from yellow to cirrus pink [14]. This gel preparation was added to the cell suspension. Following setting and incubation, gels were routinely compacted by a combination of compression and blotting using layers of mesh and paper sheets [12]. Briefly, 165-mm-thick stainless steel mesh and a layer of nylon mesh were placed on a double layer of absorbent paper. The collagen gel was placed on the nylon mesh, covered with a second nylon mesh, and loaded with a 120-g flat metal block (steel) for 5 min at room temperature, giving a flat collagen sheet (50-60 mm thick) protected between two nylon meshes. These dense sheets of collagen were then rolled to produce a tight spirally wound rod, 2.3 mm in diameter and 21 mm long. Cell densities were increased by the plastic compression in direct proportion to the volume reduction of gel and final cell density was calculated as: initial cell density×fold volume change. Hence for a typical initial gel volume of 5 ml, the percentage of collagen was 0.2%, which increased to 11% following compression (measured by dry/wet weight ratio), which corresponds to a 58-fold increase. The cell density would be expected to change by the same degree from a total of 100 000 cells/ml (or 0.5 million cells/construct) to a final density of 5.8 million cells/ml; 200 000 cells/ml (or 1 million cells/construct) to 11.6 million cells/ml; 400 000 cells/ml (or 2 million cells/construct) to 23.2 million cells/ml [15].

Oxygen Monitoring.

Figure 1:
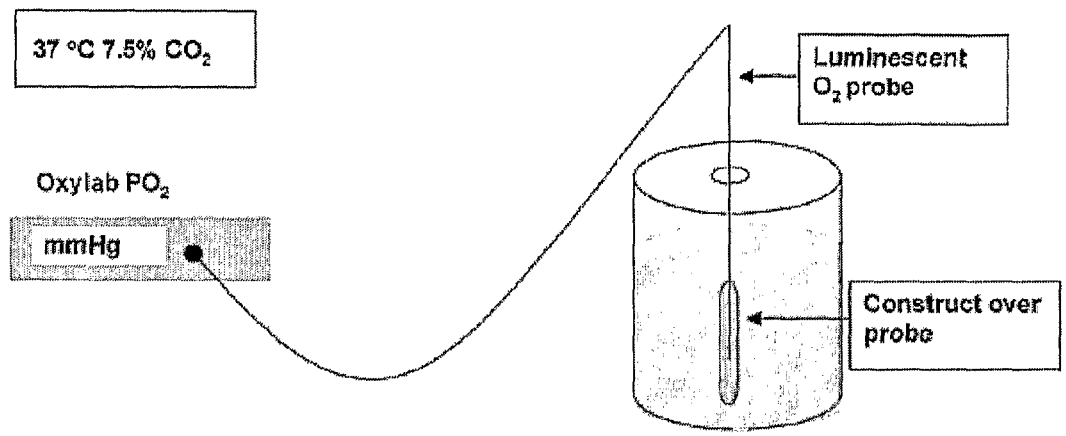
FIG. 1 shows a schematic of the experimental set up with oxygen probe in the centre of a spiralled plastic compression construct. Constructs were cultured in 50 ml media.
Figure 2:
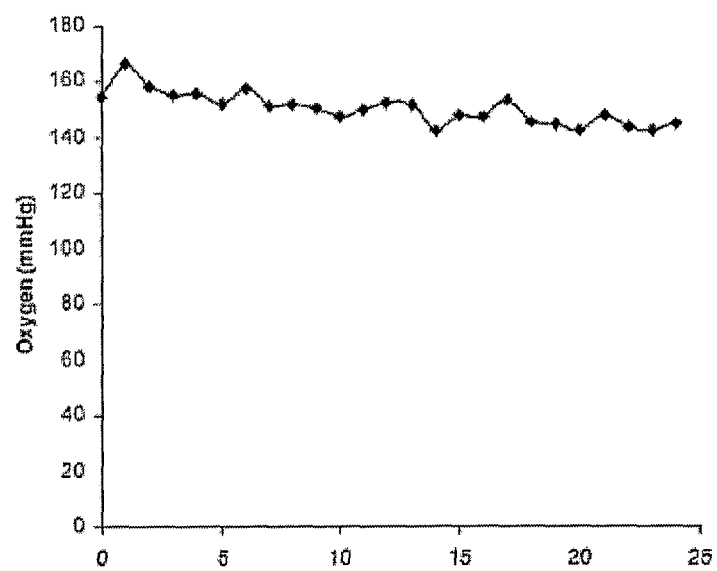
FIG. 2 shows oxygen levels in the centre of acellular plastic compression constructs.
Figure 3:
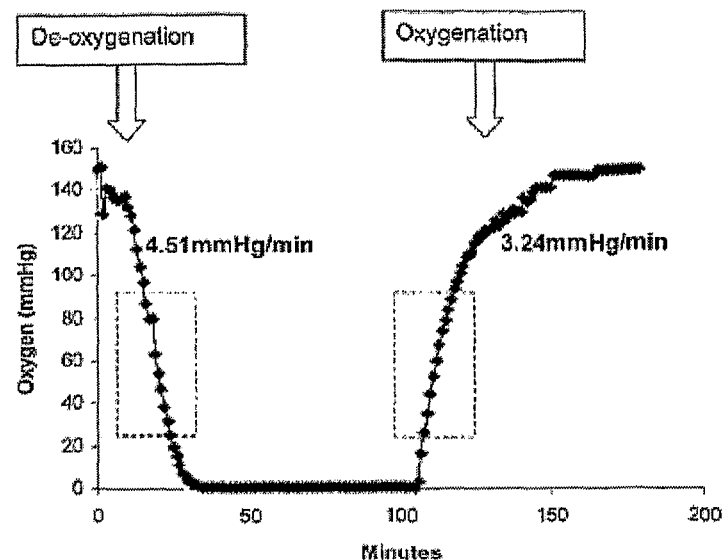
FIG. 3 shows showing the deoxygenation of an acellular plastic compression construct with sodium sulphite, followed by oxygenation in DMEM media (values of 4.5+/−0.5 and 3.2+/−0.5 mmHg/min). The gradients (corresponding to de-oxygenation and re-oxygenation rates) were estimated using the approximately linear portions of the traces.

Fibre-optic oxygen probes (Oxford Optronix, Oxford, UK) were inserted into the centre of the 3D spiral constructs and positioned halfway along its axis (FIG. 1). The constructs were then sealed at the end using cyanoacrylate glue. Hence, a diffusion length of >1 mm was studied and refers mainly to lateral diffusion, as the ends of the construct were sealed. The tip of the sensor probe (280 mm diameter) incorporates an oxygen-sensitive luminescent probe within an oxygen-permeable matrix. The luminescence is quenched in the presence of molecular oxygen so that the luminescence emission lifetime becomes longer at lower oxygen concentrations in the surrounding medium. The calibration of the probe, which is accurate to 0.7 mmHg, essentially relies on the correlation of the luminescence lifetime (rather than intensity) versus the oxygen concentration [16]. This method results in an exceptionally stable calibrated response so that each probe may be used up to 6 days at the slowest sampling rate. Therefore, for monitoring of constructs for longer than 6 days, the expiring probes were removed and new probes inserted on day 5 (see below). After each experiment, the probe reading was checked in the external medium to confirm that there was no drift in the response. The fibre-optic probes were used in conjunction with an OxyLabpO2 ETM system coupled to an A/D converter (12 bit) and the results were recorded on an IBM PC computer using Labview. Results are presented as partial pressure values, i.e., pO2 in mmHg (e.g. 7.6 mmHg corresponds to 1% oxygen). The sampling rate was varied according to the experiment performed, yielding an overall response time of <10 s (for de-oxygenation measurements, FIGS. 2, 3) and up to ~30 s for the long-term studies as shown in FIGS. 4 and 5. For studies of the rate of oxygen diffusion through the construct, we transferred the construct containing the probe into an anoxic solution of 3% sodium sulphite at 37 8 C. Rates of de-oxygenation and re-oxygenation were estimated using the quasilinear portions of the traces, as shown in FIGS. 1 to 3. Samples were kept and monitored in 7.5% CO2-enriched incubators. At the end of each experiment the construct was removed and the ambient O2 tension of the media tested, which remained at approximately 140 mmHg.

Cell Viability

Cell viability was assessed using Live/Dead Viability/Cytotoxicity Kit (Molecular Probes, L-3224) based on the simultaneous determination of live and dead cells with calcein AM and ethidium homodimer (EthD-1), respectively, for qualitative analysis. Quantitative analyses were carried out with Live/Dead Reduced Biohazard Viability/Cytotoxicity Kit (Molecular Probes, L-7013) according to the manufacturer's protocol. SYTO_ 10, a green fluorescent nucleic acid stain and Dead Red (ethidium homodimer-2) were used, and, after capturing images, live/dead nuclei were counted to ascertain percentage viability. Viability of cells in each construct was performed independently from the oxygen measurements. Representative areas for O2 determination were chosen in two regions (core and surface) of plastic compressed constructs and were visualized Cell. Mol. Life Sci. Research Article 3 with confocal microscopy (Bio-Rad Radiance 2100, Carl Zeiss Ltd, Hertfordshire, UK). Quantitative PCR analysis of VEGF mRNA. RNA extraction from experimental constructs was performed independently from the oxygen measurements. RNA was extracted either from the whole construct, or from specific regions of the spiral construct (core, mid and surface). These regions were isolated after culture by unrolling the spirals and cutting into the three different regions corresponding to core, mid and surface. Total cellular RNA was isolated from the cellular 3D plastic compressed constructs using the Qiagen RNeasymethod (Qiagen, UK). Constructs were first flash-frozen in liquid nitrogen, and 500 ml lysis buffer containing 2-mercaptoethanol was added to each sample and left to dissolve at room temperature for 40 min (Qiagen, UK). The resultant solution was then aspirated using a 21-G needle and from then on the commercial assay protocol was followed (Qiagen, UK). RNA was eluted in RNase-free water, and the concentration determined by spectrophotometry at 260 and 280 nm (Genequant, Pharmacia Biotech, NJ, USA). First strand cDNA synthesis was performed using Amplitaq reverse transcriptase (Applied Biosystems, Roche). Total RNA (0.5 mg RNA) was diluted in 38.85 ml water. A further 9.15 ml Mastermix was added to each tube (dNTP, RNase inhibitor, MgCl2, Oligo DT Random primers; Applied Biosystems, Roche), and heated at 70 8 C for 10 min; 2 ml reverse transcriptase was then added to each tube and tubes were incubated at 40 8 C for 1.5 h, followed by heating at 90 8 C for 2 min to denature any remaining enzyme.

Real-Time Quantitative PCR for VEGF

Relative quantitative PCR was performed using Applied Biosystems 7300 Real-time PCR system (CA, USA), with the Taqman universal PCR Master Mix (Applied Biosystems). cDNA, 9 ml/reaction, was mixed with 1 mL of the required gene probe (VEGF, Applied Biosystems assay ID: Hs00900057_m1 or GAPDH, Applied Biosystems assay ID: Hs99999905_m1) and 10 ml Mastermix (Applied Biosystems) in a 96-well plate for cycling and analysis in the Applied Biosystems 7300 Real-time PCR machine (total 20-ml reaction volume). The primer sequences are not disclosed and kept confidential by Applied Biosystems (Roche). Each primer set is calibrated to work optimally in the 7300 Real-time PCR machine. The combined thermal cycling and amplification-specific software enabled detection of the PCR products as cycle-by-cycle accumulation in a single-tube reaction. Values for each sample were normalised to the corresponding GAPDH result, which did not change significantly in any sample tested. Relative quantification was performed by expressing each sample/GAPDH ratio relative to a calibrator. This calibrator was set as 2 million cells per construct at 1 day. This calibrator was run along each run tested and compared.

By doing this, any small changes from run to run could be accounted for, as we were relying on relative quantification. This calibrator was measured in each PCR run (with no significant variation) and was always set to unity, and the sample change expressed as fold increase or decrease relative to this. In the case of cell density, culture period and region experiments, this was set as 2 million cells/construct at 24 h. Therefore, all relative quantification of gene expression changes were set relative to this.

Results

The 3D monitoring set-up is shown schematically in FIG. 1. Validation and calibration studies on constructs without cells (FIG. 2) showed a steady baseline level of O2 tension in the core of cell-free constructs, with negligible consumption of oxygen over 24 h (not significantly different from the external medium), consistent with minimal O2 consumption of the probe. Cell-independent depletion and recovery of core O2 levels was demonstrated (FIG. 3) by addition and then removal and washout of a 3% solution of sodium sulphite to sequester O2 from the system. The oxygen levels were observed to fall progressively over several minutes, reaching zero after approximately 30 min. Note that the time response of the probes was set to <10 s. Recovery back to air-saturated pO2 levels was measured by transferring the construct still containing the probe back into an air-saturated solution, which occurred at an approximate rate of 3.2×0.5 mmHg/min. Comparable rapid rates of reequilibration were seen using N2 saturation of medium instead of the sodium sulphite reagent. Cellular constructs exhibited time-dependent oxygen depletion in their core, where the probe was positioned, over a period of 24 h (FIG. 4). Oxygen levels fell rapidly towards approximately steady-state or plateau values, which varied according to the cell density. Cell consumption, therefore, appeared to be the only factor influencing oxygen levels in the construct. Cell density was the key determining factor in the degree of oxygen depletion response, with the lower core pO2 correlating with the higher cell density, which ranged from 0, 5.8, 11.6 to 23.2 million cells/ml. In this case, the plateau O2 tensions declined significantly ($p<0.001$) with each increase in cell density. The oxygen level in the centre of constructs seeded with 0.5 million cells (final density of 5.8 million cells/ml) was around 80 mmHg after 24 h, compared to a construct seeded with 2 million cells (final cell density of 23.2 million cells/ml), where the level was ~25 mmHg.

Exposure of cells to low levels of oxygen in the core had no effect on cell viability over this 24-h period. Cells in the construct core had over 95% viability after exposure to both 80 mmHg and 25 mmHg (FIG. 5). Hence exposure of cells to oxygen tensions as low as 25 mmHg did not increase cell death up to 5 days. At day 10, up to 55% cell death was observed in the core, compared to 40% at the surface. In such a 3D model, the diffusion of critical higher molecular weight nutrients may also be a limiting factor for cell survival. Glucose diffusion coefficients have previously been established and this is not found to be limiting for cells in the same 3D model [17].

FIG. 6 shows the core O2 profile, over a 10-day period, of a construct seeded at an initial cell density of 2 million cells (23.2 million cells/ml). Importantly, after the initial 24-h fall to a first equilibrium level of ~25 mmHg, core oxygen tension increased to a second elevated steady state of around 60 mmHg. This is likely to be a result of changes in cell consumption rather than changes in material properties (FIG. 6). Over the 10-day period, there were no major changes in cell number through proliferation. After 5 days, core cell viability was still 80%, and close to 100% at the surface. Hence, between the 30- and 36-h culture periods, the stabilised core O2 tension rose by 35 mmHg (>twofold increase), to approximately 60 mmHg. This occurred over a 6-h period, consistent with a change in fibroblast metabolism and O2 utilisation. This level was approximately maintained over the following 24 h and then fell gradually back to ~20 mmHg over the following 72 h.

Levels of VEGF mRNA expression were measured in constructs at the three cell densities studied and in the 23.2 million cells/ml construct over 10 days of culture (FIGS. 7 and 8). At the 24-h stage, the three cell densities gave relative VEGF gene expression levels with no significant difference, shown here relative to the highest cell density (FIG. 7). Over the longer 10-day period, VEGF expression levels changed dramatically in the 23.2 million cells/ml constructs (FIG. 8). Between days 1 and 3 (23.2 million cells/ml) there was a 5-fold increase in VEGF expression ($p<0.05$), followed by small incremental increases between days 3 and 7, reaching an 11-fold increase over day 1 levels ($p<0.05$). The greatest changes, however, were seen between days 7 and 8. Expression leapt by 140-fold, to a total of 151-fold greater than day 1. This was followed almost immediately by a complete collapse in expression (149-fold), such that by day 10 expression had returned back to day 1 levels. This pattern of an apparent temporal spike of growth factor expression is characteristic of control systems based on a number of different molecular elements operating in sequence, as might be expected for angiogenic stimulation. Such a spike in VEGF expression would be expected where only one growth factor of a sequential cocktail was monitored, as in this system. This pattern of VEGF regulation over 10 days was not observed with the lower cell densities studied.

Zonal changes in VEGF expression, through the thickness of the spiral constructs (23.2 million cells/ml) and so along the gradient of O2 tension, were determined at the 8-day culture stage (core, mid and surface). Zonal changes were measured by unfurling the spiral construct after culturing (FIG. 9). It was assumed that cells in the core section of the gel, which was the zone sampled by the probe, had been exposed to O2 levels between 20 and 60 mmHg, in the mid section to between 60 and 100 mmHg, and in the outer section, which was in close proximity to the aerated medium, to between 100 and 140 mmHg over most of the culture period. Significantly higher levels of VEGF were found in the core region, where cells were exposed to the lowest levels of O2. FIG. 9 shows the gradient of VEGF expression at 8 day (23.2 million cells/ml) under these conditions (i.e., the underlying zonal heterogeneity at day 8). Importantly cells in the surface region still expressed increased levels of message (4.7-fold increase over basal 1-day VEGF levels). In the mid and core regions this increased to 7.1- and 10.1-fold greater expression than 1-day levels, consistent with a direct relationship between O2 tension and VEGF gene expression. However, given high O2 tensions found in the surface zone, this provides indication that cells were either extremely sensitive to very modest reductions in available O2 or, more plausibly, surface zone cells had responded to earlier stage cytokine or metabolic signals (not measured here) produced and diffusing out from the core cells. This provides indication that systems exist for amplifying the zone of increased VEGF expression.

Current views of tissue viability and 3D cellular constructs are dominated by the ability of 'deeper lying' cells to receive sufficient nutrient and oxygen for normal activity and ultimately for survival. In intact tissues such factors are clearly controlled by the presence and rates of micro-vascular perfusion. In the absence of this process, in 3D culture, cells rely entirely on simple diffusion from the construct margins. However, there have been few, if any, effective quantitatively defined 3D models that enable testing of the interplay of matrix density and cell density on O2 depletion. As a result, concepts on cell vulnerability to low O2, together with the rate, extent and nature of their responses (short of cell death) are simplistic. Importantly, many are based on tumour or other cell masses, with little or no extracellular matrix content. The present study has developed the first 3D-monitored model of connective tissue to define precisely which factors dominate and how they affect resident cell behaviour and survival. Using this model, the time-dependence of oxygen versus VEGF was studied over several days together with spatial measurements.

There are several key determining factors in this system, as there are in vivo, for the level and rate of attainment of minimum O2 tension at the core (furthest from perfusion point) of 3D constructs and tissues: (1) cell density, which is assumed to be a homogenous distribution, but can change zonally and over time, (2) matrix density/permeability to the limiting diffusing component (O2 or other nutrient), and (3) cell type or cell activity (i.e., O2 demand of the cells, which is dependent on aerobic/anaerobic and active/quiescent status; e.g., chondrocyte, dermal fibroblast, myoblast). The plastic compression process for the 3D collagen constructs provides control of all these factors. The cell and matrix densities are both determined by the initial inoculum and initial collagen content (respectively) multiplied by the fold compression ($\times 58$). The collagen matrix has a nano-fibrillar lattice of around 88% water, making it highly permeable to O2.

The initial rate of consumption of O2 was non-linear over the first 10-30 min of the experiment, but thereafter was nearly constant. In this system the rate of fall of O2 and the equilibrium consumption of O2 was entirely predictive, being dependent on cell density (FIG. 4). Despite the relatively high matrix density and resultant O2 depletion at the centre of the constructs, cell viability was unaffected at 24 h and only slightly reduced (>80% of cells viable) after 5 days at the highest cell density (FIG. 6). To relate this to other work on cell responses to low levels of O2, pathological hypoxia is conventionally set at <1% or 8 mmHg [6, 18]. Consequently, pO2 levels in the core of high cell density constructs here never fell below 18 mmHg, and so were not conventionally hypoxic (FIG. 6). This challenges the conventional impression that diffusion gradients >1 mm are frequently damaging to cells, but supports the idea that dense fibrillar collagen represents only a modest diffusion barrier (i.e., highly permeable to small molecules). This high permeability to O2 is reasonable given the nano-fibrillar mesh structure of the matrix, with approximately 88% fluid phase. This was established here by the O2 re-equilibrium rate (1-mm shortest diffusion path) of $4.5 \times 0.5$ mmHg/min.

Importantly, the greater reductions in core O2 tension were apparently cell number dependent, providing indication that it is not necessarily matrix diffusion path length that dominates cell response, but the number of overlying cell layers, each depleting O2. This provides an insight into understanding why the core of cell-rich, matrix-poor structures (tumours, organs) are so much more vulnerable to core cell necrosis compared to connective tissues. The overall levels of VEGF measured in the different regions were significantly lower compared to the total day 8 reading. This may be due to slow processing of the constructs since they had to be unrolled carefully, during which time (up to 1 h) the values of VEGF may have dropped as cells in the entire construct became exposed to normoxia, including the core region during the final stage of unrolling. Cells exposed to low oxygen tensions respond by significant increases in TGF-b, platelet-derived growth factor (PDGF) and VEGF expression. It seems likely, therefore, that some exposure to low levels of oxygen is in fact complementary to tissue construct maturation, and will in fact be beneficial to cell survival. The influence of varying O2 tension on cellular proliferation and differentiation is crucial in understanding how physiological microenvironments can influence cellular behaviour, and there has been work to show that low levels of oxygen enhance proliferation of many cell types, including fibroblasts [22, 23]. Cell growth at reduced O2 tension does not necessarily result in cell death. When cultured at 2% oxygen (~15.2 mmHg), trophoblast cell proliferation is stimulated, whereas at 20% (152 mmHg), cells actually exit the cell cycle, and undergo increased differentiation [22]. Reduced O2 tensions measured in the current study (down to as low as 15 mmHg), were close to those used in the study by Ma et al. [22], and while direct extrapolation is dangerous here, due to differences in cell type and cell density, some parallels can be drawn. For instance, it does highlight the paradox of suggestions that 3D cell/matrix culture composites may undergo cell death in the centre due to oxygen depletion, in contrast to data indicating that reduced levels of O2 tension in tissue culture can enhance cell proliferation and indeed mimic many native cell environments. Precise and 3D-localised measurement of O2 tension is, therefore, critical in determining our understanding of any given 3D tissue model. It may, for example, be necessary to manipulate both high and low levels of oxygen locally to stimulate at different stages cell proliferation and cell differentiation for maturation of the model.

The first of three cell reactions to prolonged low O2 tension (>24 h, high density) was an apparent shift to anaerobic metabolism, indicated by the relative increase in O2 tension after 23 h (FIG. 4). Although confirmation of this was beyond the scope of this study, such a shift to predominantly glycolytic metabolism seems the most reasonable explanation, given that changes in cell number or matrix permeability capable of explaining this rise in core O2 can be ruled out in this instance. Such a concerted shift in cell metabolism would not be surprising. It does, however, provide indication that such cells have low O2 responses, even above conventional pathological hypoxia and these this may trigger further downstream responses. Most tissue repair and tissue engineering integration processes depend on rapid angiogenesis, triggered by a number of angiogenic proteins, including VEGF.

VEGF expression is induced by the transcription factor HIF-1a, which possesses an oxygen-sensitive degradation domain [24, 25]. Large increases in VEGF mRNA levels were measured by day 8 in cell-dense constructs. One trigger for this up-regulation may be low levels of O2 or a resultant sustained period of glycolytic metabolism [26]. Confirmation that cell death was not significant here (>80% cell viability at day 5) is important, since it indicates that the VEGF response was not dependent on dying cells. However, by day 10, a reduction in cell viability was measured and this has been the predominant reason VEGF levels dropped on day 10. Furthermore, it was possible to demonstrate that much (although not all) of the VEGF response was due to cells at the construct core, where levels were assumed to range between 20 and 60 mmHg compared to 100 and 140 mmHg at the construct surface. This was achievable because as the 3D spiral model could be unfurled, following the oxygen measurements, which then allowed us to quantitatively map out where VEGF production was up-regulated, with regards to the spatial position. The exposure of cells to O2 was dependent on the specific region they were located within the gel construct, which correspondingly influenced VEGF levels. Critically, the up-regulation of VEGF was not observed up to 24 h, when constructs were seeded with different cell densities (and therefore exposed to different O2 gradients within the constructs). The gradients varied from 82 to 140 mmHg (0.5 million), 66 to 140 mmHg (1 million), and 23 to 140 mmHg (2 million). This controlled in vitro system allowed the O2-dependent VEGF regulation to be monitored carefully. As levels of O2 did not fall below 15 mmHg, and certainly not as low as 7.6 mmHg (1% oxygen), it cannot be said that the trigger for VEGF up-regulation is classical "pathological hypoxia". The signalling of this low level of O2 (within physiological hypoxia range) to the cells to stimulate VEGF is therefore likely to be through initial up-regulation of its transcription factor, HIF-Ia.

To assess the effect of in vitro pre-conditioning on angiogenic implants, 3D collagen constructs were produced as described above and seeded with $2\times10^6$ human dermal fibroblasts (HDFs). The amounts of angiogenesis factors HIF-1a and VEGF in the constructs after 5 and 10 days in in vitro culture were measured by ELISA. High levels of both HIF-1a and VEGF were observed in the constructs after in vitro culture (FIGS. 11 and 12). Neither HIF-1a nor VEGF was observed by ELISA in control gels which had not been cultured in vitro.

To assess the effect of angiogenic implants containing live cells in vivo, 3D collagen constructs were produced as described above and seeded with $2\times10^6$ human dermal fibroblasts (HDFs) (equivalent to $23\times10^6$ cells/ml). The constructs were either pre-conditioned for 5 days in vitro or not preconditioned. The constructs were then embedded into acellular collagen wraps and subcutaneously implanted into rabbits (subcutaneously). After 1 week, the constructs were recovered (see FIG. 13). Ingrown vessels were observed from the host into both the pre-conditioned and non-pre-conditioned constructs, indicating that both types of constructs simulate angiogenic responses in the rabbit host. Vascularisation was observed to be increased in the pre-conditioned constructs, relative to the non-pre-conditioned constructs.

The above experiments were then repeated with 3D collagen constructs seeded with $5\times10^5$ human dermal fibroblasts (HDFs) (equivalent to $5\times10^6$ cells/ml). The constructs were either pre-conditioned for 5 days in vitro or not preconditioned. The constructs were then embedded into acellular collagen wraps and subcutaneously implanted into rabbits (subcutaneously). After 1 week, the constructs were recovered and assessed for vascularisation. Vascularisation of the constructs which had been preconditioned in vitro was observed. No vascularisation occurs in constructs containing $5\times10^5$ cells which have not been pre-conditioned.

In a control experiment, a 3D collagen construct which did not contain cells was subcutaneously implanted into rabbits. After 1 week, the acellular construct was recovered and assessed for vascularisation. No vascularisation was observed.

To assess the effect of angiogenic implants without live cells in vivo, 3D collagen constructs were produced as described above and seeded with $2\times10^6$ human dermal fibroblasts (HDFs) (equivalent to $23\times10^6$ cells/ml). The constructs were either not preconditioned (controls) or pre-conditioned by culturing for 10 days in vitro, and then all constructs were frozen for 5 mins in liquid nitrogen, embedded into acellular collagen wraps and subcutaneously implanted into rabbits (subcutaneously). After 1 week, the constructs were recovered. No visible vascularisation was observed in the control constructs which had not been pre-conditioned (FIG. 14). By contrast, visible ingrowth of the host vasculature into collagen implants which had been preconditioned before freezing was observed (FIG. 15).

Angiogenesis was therefore shown to be promoted by both cellular and acellular angiogenic implants as described herein.

In summary, we have established a basic model for the study of O2 consumption by human dermal fibroblasts in 3D collagen matrices. It was clearly evident that no adverse affect on cell viability was observed due to lower levels of oxygen exposure. In turn, the pattern of VEGF regulation has been determined under low pO2 but non-hypoxic conditions. This study also shows that naturally occurring angiogenic signals may be engineered for induction of vascularisation in such 3D tissue engineered constructs post implantation. The production of VEGF, along with other cell-manufactured angiogenic signals, in a 3D construct core, with lower levels produced by cells the closer they got to the surface, a gradient of these signals would induce vascularisation from the surface of a 3D construct towards the core, potentially inducing vascularisation from outside the construct in an in vivo scenario. For instance, by understanding when and where cells at defined densities and within a defined matrix will up-regulate VEGF production could be used to promote implant integration in vivo.

REFERENCES

1 Weaver, V. et al. (1997) J. Cell Biol. 137, 231-245.

2 Wang, F. et al (1998) Proc. Natl. Acad. Sci. USA 95, 14821-14826.

3 Weiss, P. (1959) Cellular dynamics. Rev. Mod. Phys. 31, 11-20.

4 Tomasek, J. J et al. (2002) Nat. Rev. Mol. Cell. Biol. 3, 349-363.

5 Grinnell, F. (2003). Trends Cell Biol. 13, 264-269.

6 Okazaki, K. M. and Maltepe, E. (2006) Regen. Med. 1, 71-83.

7 Werrlein, R. J. and Glinos, A. D. (1974) Nature 251, 317-319.

8 Tokuda, Y. et al (2000) J. Cell Physiol. 182, 414-420.

9 Gnaiger, E. et al (2000) Proc. Natl. Acad. Sci. USA 97, 11080-11085.

10 Levenberg, S. et al (2005) Nat. Biotechnol. 23, 879-884.

11 Lussi, J. W. et al (2006). Biomaterials 27, 2534-2541.

12 Brown, R. A. et al. (2005) Adv. Funct. Mater. 15, 1762-1770.

13 Burt, A. and McGrouther, D. A. (1992) Production and use of skin cell cultures in therapeutic situation. In: Animal Cell Biotechnology, vol. 5, pp. 150-168, Spier, R. E., Griffiths, J. B. (eds.), Academic Press, New York.

14 Cheema, U. et al (2003) Cell Motif. Cytoskeleton 54, 226-236.

15 Cheema, U. et al. (2007. Biotechnol. Bioprocess. Eng. 12, 9-14.

16 Seddon, B. M. et al (2001) Radiat. Res. 155, 837-846.

17 Rong, Z., et al (2006). Analyst 131, 816-821.
18 Cooper, A. and Beasley, D. (1999) Am. J. Physiol. 277, H1326-H1337.
19 Falanga, V. et al (1991). J. Invest. Dermatol. 97, 634-637.
20 Kourembanas, S., et al (1990) J. Clin. Invest. 86, 670-674.
21 Steinbrech, D. S et al (1999) J. Surg. Res. 84, 127-133.
22 Ma, T. et al (2001) Tissue Eng. 7, 495-506.
23 Falanga, V. and Kirsner, R. S. (1993) J. Cell Physiol. 154, 506-510.
24 Trentin, D. et al. (2006) Proc. Natl. Acad. Sci. USA 103, 2506-2511.
25 Semenza, G. L. (1998) Curr. Opin. Genet. Dev. 8, 588-594.
26 Kumar, V. B. et al. (2007) J. Cell Physiol. 211, 477-485.
27. Mudera V. et al *J Tissue Eng Regen Med* 2007; 1: 192-198.

The invention claimed is:

1. A mammalian cell culture comprising:
a scaffold comprising a gel having a pocket on the surface thereof; and mammalian cells,
said mammalian cells being located in the pocket,
wherein said gel comprises a matrix of scaffold fibres and an interstitial aqueous liquid, said gel being produced by the coalescence of the fibrils to form a continuous network around the aqueous interstitial liquid, and wherein,
said pocket is produced by contacting the surface of the gel with a die having a projection on the surface thereof, such that said projection embosses the pocket in the surface of the gel, wherein the pocket is at least 50 μm deep.

2. A mammalian cell culture according to claim 1 wherein the gel is a collagen gel.

3. A mammalian cell culture comprising:
a scaffold comprising a gel having a pocket on the surface thereof; and mammalian cells
said mammalian cells being located in the pocket,
wherein said gel comprises a matrix of scaffold fibres and an interstitial aqueous liquid, said gel being produced by the coalescence of the fibrils to form a continuous network around the aqueous interstitial liquid, and wherein,
said pocket is produced by contacting the surface of the gel with a die having a projection on the surface thereof, such that said projection embosses the pocket in the surface of the gel, wherein the pocket is 200 μm to 5000 μm deep.

4. A mammalian cell culture according to claim 1 wherein the pocket is 50 to 2000 μm in diameter.

5. A mammalian cell culture according to claim 1 wherein greater than 5 million cells per ml are located in the pocket.

6. A mammalian cell culture according to claim 1 wherein the mammalian cells are stem cells.

7. A mammalian cell culture according to claim 6 wherein the stem cells are selected from the group consisting of corneal stem cells; skin epidermal stem cells; gut stem cells; orogenital stem cells; epithelial stem cells; bone marrow stromal stem cells; and growth plate stem cells.

8. A mammalian cell culture according to claim 1 wherein the pocket contains only cells.

9. A mammalian cell culture according to claim 1 wherein said mammalian cells produce concentration gradients of diffusible factors and waste metabolites within the pocket.

10. A mammalian cell culture according to claim 9 wherein said concentration gradients stimulate the differentiation and proliferation of cells in the pocket.

* * * * *